(12) United States Patent
Henry

(10) Patent No.: US 8,939,035 B2
(45) Date of Patent: *Jan. 27, 2015

(54) MULTIPHASE METERING SYSTEM

(71) Applicant: Invensys Systems Inc., Foxboro, MA (US)

(72) Inventor: Manus P. Henry, Oxford (GB)

(73) Assignee: Invensys Systems, Inc., Foxboro, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/084,308

(22) Filed: Nov. 19, 2013

(65) Prior Publication Data

US 2014/0076035 A1  Mar. 20, 2014

Related U.S. Application Data

(63) Continuation of application No. 13/215,979, filed on Aug. 23, 2011, now Pat. No. 8,621,937.

(60) Provisional application No. 61/376,589, filed on Aug. 24, 2010, provisional application No. 61/405,944, filed on Oct. 22, 2010.

(51) Int. Cl.
G01F 1/84 (2006.01)
G01N 33/28 (2006.01)
G01F 1/74 (2006.01)
G01F 15/02 (2006.01)

(52) U.S. Cl.
CPC .............. *G01N 33/2847* (2013.01); *G01F 1/74* (2013.01); *G01F 1/8436* (2013.01); *G01F 1/8486* (2013.01); *G01F 15/024* (2013.01)
USPC .................................................. 73/861.354

(58) Field of Classification Search
USPC ...................... 73/861.355–861.357
See application file for complete search history.

(56) References Cited

U.S. PATENT DOCUMENTS 8,621,937 B2 * 1/2014 Henry ...................... 73/861.354

* cited by examiner

Primary Examiner — Jewel V Thompson
(74) Attorney, Agent, or Firm — Thomas J. Roth, Esq.

(57) ABSTRACT

A multi-phase fluid is passed through a Coriolis flowmeter and a watercut meter. The multi-phase fluid includes two phases during a first time period and three phases during a second time period. It is determined that the multi-phase fluid includes two phases during the first time period, and a first value of a parameter of the multi-phase fluid is determined using a value measured by the Coriolis flowmeter during the first time period. A second value of a parameter of the multi-phase fluid is determined using a value measured by the watercut meter during the first time period. The first value is compared to the second value, and it is determined, based on the comparison, that the first value and the second value are inconsistent with each other.

17 Claims, 9 Drawing Sheets

MULTIPHASE METERING SYSTEM

CROSS-REFERENCE TO RELATED APPLICATIONS

This application is a continuation of and claims priority to U.S. application Ser. No. 13/215,979, entitled MULTIPHASE METERING SYSTEM, filed Aug. 23, 2011 now issued as U.S. Pat. NO. 8,621,937, which claims the benefit of U.S. Provisional Application No. 61/376,589, filed Aug. 24, 2010, and titled MULTIPHASE METERING SYSTEM, and U.S. Provisional Application No. 61/405,944, filed Oct. 22, 2010 and titled MULTIPHASE METERING SYSTEM. The disclosure of these provisional applications are incorporated by reference in their entirety.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, density flowmeters, or densitometers, provide a measurement of the density of material flowing through a conduit. Mass flowmeters also may provide a measurement of the density of the material.

For example, Coriolis-type mass flowmeters are based on the Coriolis effect, in which material flowing through a rotating conduit is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

In one general aspect, a method includes passing a multi-phase fluid through a Coriolis flowmeter, the multi-phase fluid including two phases during a first time period and three phases during a second time period, passing the multi-phase fluid through a watercut meter, determining that the multi-phase fluid includes two phases during the first time period, determining a first value of a parameter of the multi-phase fluid using a value measured by the Coriolis flowmeter during the first time period, determining a second value of a parameter of the multi-phase fluid using a value measured by the watercut meter during the first time period, comparing the first value to the second value, and determining, based on the comparison, that the first value and the second value are inconsistent with each other.

Implementations may include one or more of the following features. The parameter may be a density of the multi-phase fluid, and the first value is a first density value and the second value is a second density value. The second density may be determined using $$\rho_{mW} = \frac{\delta_{wW}}{100} * \rho_w + \left(1 - \frac{\delta_{wW}}{100}\right) * \rho_o,$$

where $\rho_o$ is an assumed oil density, $\rho_w$ is an assumed water density, $$\delta_{wC} = \frac{(\rho_m - \rho_o)}{(\rho_w - \rho_o)} \times 100\%$$

is an estimate of the watercut, and $\rho_m$ is the first density of the multi-phase fluid measured by the Coriolis flowmeter. The parameter may be a water cut of the multi-phase fluid, and the first value is a water cut measured by the water cut meter, and the second value is a water cut determined using values read from the Coriolis flowmeter.

Comparing the first density value to the second density value may include determining a percentage difference between the first density value and the second density value. In some implementations, it may be determined that an error exists in the watercut meter based on the inconsistency, or it may be determined that an error exists in the Coriolis flowmeter based on the inconsistency. At least one of the assumed oil density or the assumed water density may be determined to be inaccurate based on the inconsistency. During the first time period, the multi-phase fluid may be purely liquid. Determining, based on the comparison, that the first value and the second value are inconsistent with each other may include determining that a percentage difference between the first value and the second value exceeds a threshold. The threshold may be about 5%.

In another general aspect, a system includes a watercut meter configured to receive a fluid, and a Coriolis flowmeter coupled to the watercut meter. The Coriolis flowmeter is configured to receive the fluid, and the flowmeter is oriented such that the fluid flows downward through the Coriolis flowmeter.

Implementations may include one or more of the following features. The system also may include a computing device configured to determine that the multi-phase fluid includes two phases during the first time period, determine a first value of a parameter of the multi-phase fluid using a value measured by the Coriolis flowmeter during the first time period, determine a second value of a parameter of the multi-phase fluid using a value measured by the watercut meter during the first time period, compare the first value to the second value, and determine, based on the comparison, that the first value and the second value are inconsistent with each other. The computing device may be a processor included in a transmitter coupled to the Coriolis flowmeter. The computing device may be a processor included in a flow computer external to the Coriolis flowmeter and the water cut meter.

In some implementations, the parameter may include density of the multi-phase fluid, and the first value is a first density value and the second value is a second density value. The second density may be determined using $$\rho_{mW} = \frac{\delta_{wW}}{100} * \rho_w + \left(1 - \frac{\delta_{wW}}{100}\right) * \rho_o,$$

where $\rho_o$ is an assumed oil density, $\rho_w$ is an assumed water density, $$\delta_{wC} = \frac{(\rho_m - \rho_o)}{(\rho_w - \rho_o)} \times 100\%$$

is an estimate of the watercut, and $\rho_m$ is the first density of the multi-phase fluid measured by the Coriolis flowmeter. The parameter may include a water cut of the multi-phase fluid, and the first value is a water cut measured by the water cut meter, and the second value is a water cut determined using values read from the Coriolis flowmeter.

To compare the first density value to the second density value, the computing device may be configured to determine a percentage difference between the first density value and the second density value. In some implementations, it may be determined, based on the inconsistency, that an error exists in the watercut meter. The computing device may be further configured to determine, based on the inconsistency, that an error exists in the Coriolis flowmeter. The computing device may be further configured to determine, based on the inconsistency, that at least one of the assumed oil density or the assumed water density is inaccurate. To determine, based on the comparison, that the first value and the second value are inconsistent with each other, the computing device may be configured to determine that a percentage difference between the first value and the second value exceeds a threshold. The threshold may be about 5%. The multi-phase fluid during the first time period may be purely liquid. The water cut meter may be a liquid fraction probe.

Implementations of any of the techniques described above may include a method or process, a system, a flowmeter, or instructions stored on a storage device of a flow meter transmitter. Details of particular implementations are set forth in the accompanying drawings and description below. Other features will be apparent from the following description, including the drawings, and the claims.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow (e.g., a flow containing a mixture of liquid and gas).

Although digital flowmeters are specifically discussed below with respect to, for example, FIGS. 1 and 2, it should be understood that analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a Coriolis flowmeter system uses various control systems and related elements to measure a mass flow, density, and/or other parameters of a material(s) moving through a flowtube or other conduit.

Figure 1A:
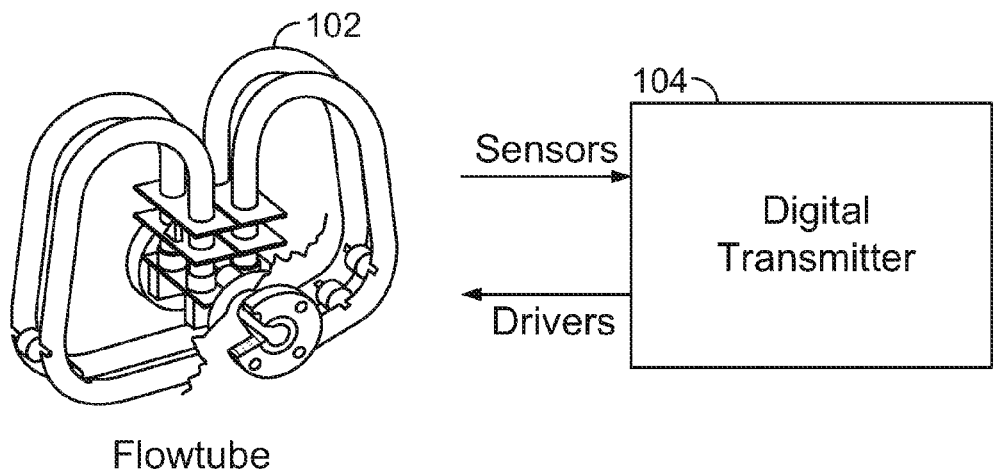
FIG. 1A is an illustration of a Coriolis flowmeter using a bent flowtube.

FIG. 1A is an illustration of a digital flowmeter using a bent flowtube 102. Specifically, the bent flowtube 102 may be used to measure one or more physical characteristics of, for example, a (traveling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the digital transmitter 104 being used with a bent flowtube are provided in, for example, commonly-assigned U.S. Pat. No. 6,311,136.

Figure 1B:
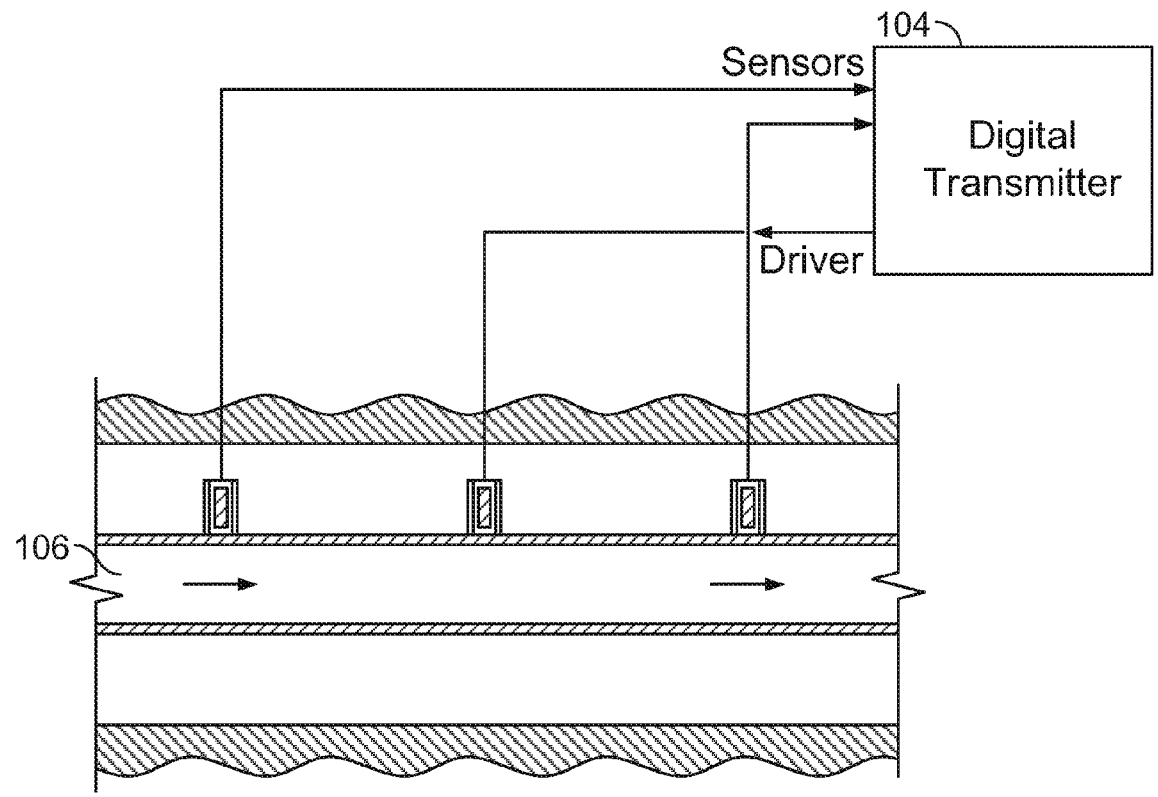
FIG. 1B is an illustration of a Coriolis flowmeter using a straight flowtube.

FIG. 1B is an illustration of a digital flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz. The bent flowtube 102 represents flowtubes having a variety of diameters, and may be operated in multiple orientations, such as, for example, in a vertical or horizontal orientation.

Figure 2:
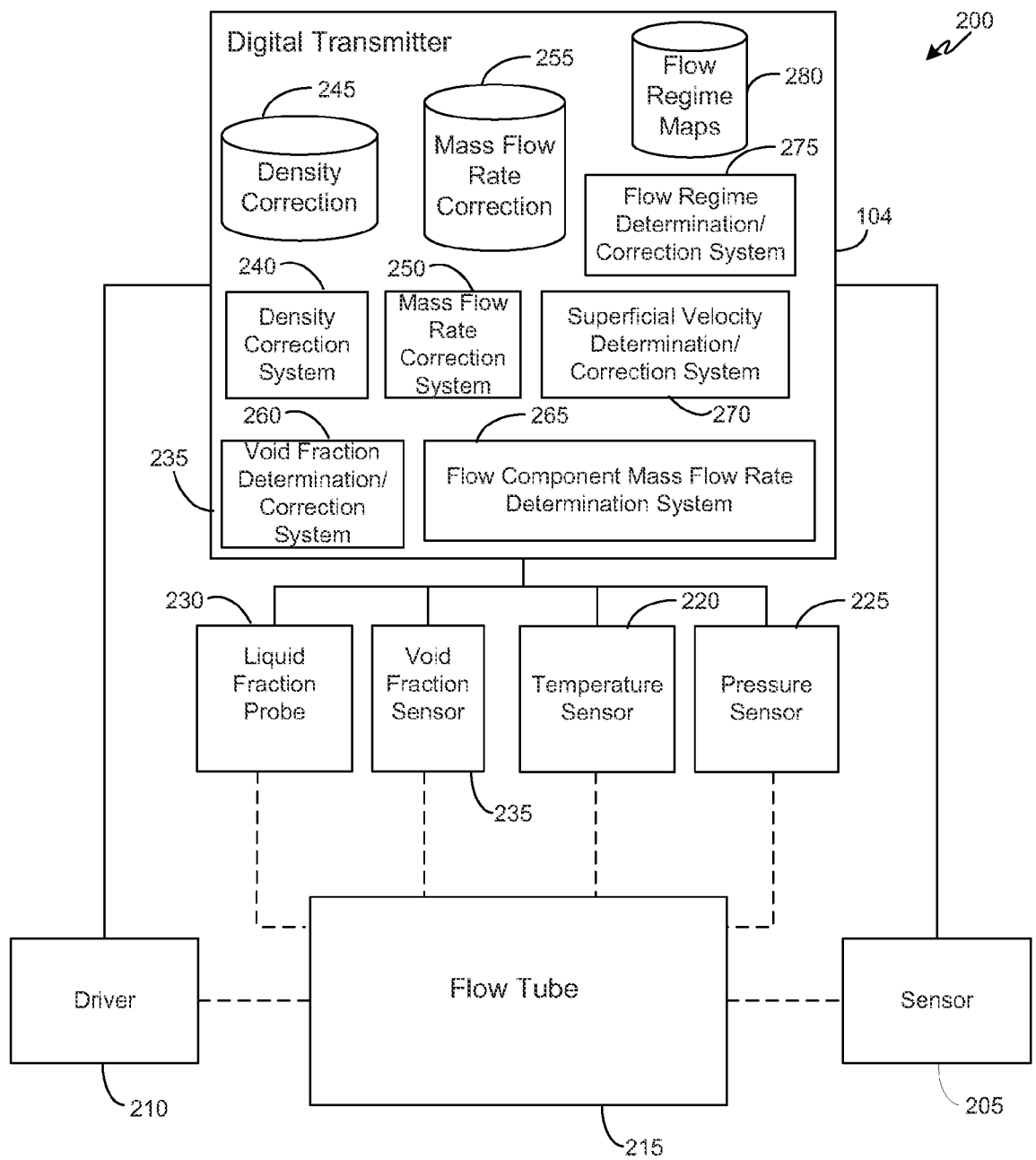
FIG. 2 is a block diagram of a Coriolis flowmeter.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a temperature sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. It should be understood that, as described in U.S. Pat. No. 6,311,136, associated digital-to-analog converters may be included for operation of the drivers 210, while analog-to-digital converters may be used to convert sensor signals from the sensors 205 for use by the digital transmitter 104.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

It should be understood that both the pressure of the fluid entering the flowtube 215 and the pressure drop across relevant points on the flowtube may be indicators of certain flow conditions. Also, while external temperature sensors may be used to measure the fluid temperature, such sensors may be used in addition to an internal flowmeter sensor designed to measure a representative temperature for flowtube calibrations. Also, some flowtubes use multiple temperature sensors for the purpose of correcting measurements for an effect of differential temperature between the process fluid and the environment (e.g., a case temperature of a housing of the flowtube). As discussed in more detail below, one potential use for the inlet fluid temperature and pressure measurements is to calculate the actual densities of a liquid and gas in a two-phase flow, based on predefined formulae.

A liquid fraction probe 230 refers to a device for measuring a volume fraction of liquid, e.g., water, when a liquid in the flowtube 215 includes water and another fluid, such as oil. Of course, such a probe, or similar probes, may be used to measure the volume fraction of a fluid other than water, if such a measurement is preferred or if the liquid does not include water. In the below description, a measured liquid is generally assumed to be water for the purposes of example, so that the liquid fraction probe 230 is generally referred to as a water fraction probe 230, or a water-cut probe 230.

A void fraction sensor 235 measures a percentage of a material in the flowtube 215 that is in gaseous form. For example, water flowing through the flowtube 215 may contain air, perhaps in the form of bubbles. Such a condition, in which the material flowing through the flowtube 215 contains more than one material is generally referred to as "two-phase flow." In particular, the term "two-phase flow" may refer to a liquid and a gas; however, "two-phase flow" also may refer to other combinations of materials, such as two liquids (e.g., oil and water).

Various techniques, represented generally in FIG. 2 by the void fraction sensor 235, exist for measuring the gas void fraction in a two-phase flow of liquid and gas (where the gas void fraction may be considered as the proportion of gas by volume in the mixture, for example expressed as a percentage). For example, various sensors or probes exist that may be inserted into the flow to determine a gas void fraction. As another example, a venturi tube (i.e., a tube with a constricted throat that determines fluid pressures and velocities by measurement of differential pressures generated at the throat as a fluid traverses the tube), relying on the fact that gas generally moves with a higher velocity than liquid(s) through a restriction, may be used to determine a pressure gradient and thereby allow a determination of the gas void fraction.

Measurements of gas void fractions also may be obtained using equipment that is wholly external to the flowtube. For example, sonar measurements may be taken to determine gas void fraction. As a specific example of such a sonar-based system, the SONARtrac™ gas void fraction monitoring system produced by CiDRA Corporation of Wallingford, Conn. may be used.

In this description, an amount of gas in a flowing fluid, measured by the void fraction sensor or otherwise determined, may be referred to as void fraction or $\alpha$, and is defined as $\alpha$=volume of gas/total volume=volume of gas/(volume of liquid+volume of gas). Accordingly, a quantity referred to herein as the liquid fraction is defined as $1-\alpha$.

In many applications where mass flow measurements are required, the void fraction of the flow can be as high as 20, 30, 40% or more. However, even at very small void fractions of 0.5%, the fundamental theory behind the Coriolis flowmeter becomes less applicable. Moreover, a presence of gas in the fluid flow also may affect both an actual and a measured value of a density of the fluid flow, generally causing the density measurement to be, and to read, lower than if the fluid flow contained only the liquid component. That is, it should be understood that a density $\rho_{liquid}$ of a liquid flowing by itself through a flowtube will be higher than an actual density $\rho_{true}$ of a two-phase flow containing the liquid and a gas, since a density of the gas (e.g., air) will generally be lower than a density of the liquid (e.g., water) in the two-phase flow. In other words, there is a density reduction when gas is added to a liquid flow that previously contained only the liquid.

Beyond this physical phenomenon, a Coriolis flowmeter measuring a two-phase fluid flow containing gas may output a density reading $\rho_{apparent}$ that is an ostensible measurement of the bulk density of the two-phase flow (e.g., of the water and air combined). This raw measurement $\rho_{apparent}$ will generally be different (lower) than the actual bulk density $\rho_{true}$ of the two-phase flow. For example, the resonant frequency used by the flowmeter may be correct for a situation in which only the liquid component is present, but, due to relative motion of the gas in the fluid flow, which serves to mask an inertia of the flowtube (i.e., causes an amount of inertia to be less than would be expected for a liquid-only flow), the density measurement may read low.

It should be understood that many conventional prior art flowmeters were unconcerned with this problem, since most such Coriolis flowmeters fail to continue operating (e.g. stall or output inaccurate measurements) at even the slightest amounts of void fraction.

U.S. Pat. No. 6,505,519, which is incorporated by reference above, discloses that such a variation of $\rho_{apparent}$ (i.e., an indicated bulk density reading of a two-phase flow that is output by a Coriolis flowmeter) from $\rho_{true}$ (i.e., an actual bulk density of the two-phase flow) may be characterized by a variety of techniques. As a result, a measured $\rho_{apparent}$ may be corrected to obtain an actual bulk density $\rho_{corrected}$, which is, at least approximately, equal to $\rho_{true}$. Somewhat similarly, an indicated bulk mass flow rate $MF_{apparent}$ (i.e., a mass flow rate of the entire two-phase flow) measured by a Coriolis flowmeter may be different by a predictable or characterizable amount from an actual bulk mass flow rate $MF_{true}$. It should be understood that correction techniques for corrected bulk mass flow rate $MF_{true}$ may be different than the techniques for correcting for density. For example, various techniques for correcting a measured $MF_{apparent}$ to obtain an actual $MF_{true}$ (or, at least, $MF_{corrected}$) are discussed in U.S. Pat. No. 6,505,519.

Examples of detailed techniques for correcting $\rho_{apparent}$ and $MF_{apparent}$ are discussed in more detail below and are also discussed in U.S. Pat. Nos. 7,059,199; 7,188,534; and 7,188,534, all of which are hereby incorporated by reference. Generally speaking, though, with respect to FIG. 2, the digital transmitter is shown as including a density correction system 240, which has access to a density correction database 245, and a mass flow rate correction system 250, which has access to a mass flow correction database 255. As discussed in more detail below, the databases 245 and 255 may contain, for example, correction algorithms that have been derived theoretically or obtained empirically, and/or correction tables that provide corrected density or mass flow values for a given set of input parameters. The databases 245 and 255 also may store a variety of other types of information that may be useful in performing the density or mass flow corrections. For example, the density correction database may store a number of densities $\rho_{liquid}$ corresponding to particular liquids (e.g., water or oil).

Further in FIG. 2, a void fraction determination/correction system 260 is operable to determine a void fraction of a two-phase flow including a liquid and a gas. In one implementation, for example, the void fraction determination/correction system 260 may determine an actual void fraction $\alpha_{true}$ from the corrected density $\rho_{corrected}$. In another implementation, the void fraction determination/correction system 260 may input an apparent or indicated void fraction measurement obtained by the void fraction sensor 235, and may correct this measurement based on an error characterization similar to the density and mass flow techniques referred to above. In another implementation, the void fraction sensor 235 may be operable to directly measure an actual void fraction $\alpha_{true}$, in which case the void fraction determination/correction system 260 simply inputs this measurement.

Once the factors of $\rho_{corrected}$, $MF_{corrected}$, and $\alpha_{corrected}$ have been determined, and perhaps in conjunction with other known or discoverable quantities, a flow component mass flow rate determination system 265 may operate to simultaneously determine a mass flow rate for the liquid phase component and a mass flow rate for the gas phase component. That is, the transmitter 104 is operable to determine individual flowrates $MF_{liquid}$ and $MF_{gas}$ of the flow components, as opposed to merely determining the bulk flowrate of the combined or total two-phase flow $MF_{true}$. Although, as just referred to, such measurements may be determined and/or output simultaneously, they also may be determined separately or independently of one another. Once the component flow rates $MF_{liquid}$ and $MF_{gas}$ have been determined in the manner generally outlined above, these initial determinations may be improved upon by a process that relies on superficial velocities of the flow components, slip velocities between the components, and/or an identified flow regime of the flow. In this way, improved values for flow rates $MF_{liquid}$ and $MF_{gas}$ may be obtained, or may be obtained over time as those flow rates change.

Superficial velocities are referred to herein as those velocities that would exist if the same mass flow rate of a given phase was traveling as a single phase through the flowtube 215. A superficial velocity determination/correction system 270 is included in the transmitter 104 for, for example, determining an apparent or corrected superficial velocity of a gas or liquid in the two-phase flow. Slip velocities refer to a condition in which gas and liquid phases in a two-phase flow have different average velocities. That is, an average velocity of a gas $AV_{gas}$ is different from an average velocity of a liquid $AV_{liquid}$. As such, a phase slip S may be defined as $S=AV_{gas}/AV_{liquid}$.

A flow regime is a term that refers to a characterization of the manner in which the two phases flow through the flowtube 215 with respect to one another and/or the flowtube 215, and may be expressed, at least partially, in terms of the superficial velocities just determined. For example, one flow regime is known as the "bubble regime," in which gas is entrained as bubbles within a liquid. As another example, the "slug regime" refers to a series of liquid "plugs" or "slugs" separated by relatively large gas pockets. For example, in vertical flow, the gas in a slug flow regime may occupy almost an entire cross-sectional area of the flowtube 215, so that the resulting flow alternates between high-liquid and high-gas composition. Other flow regimes are known to exist and to have certain defined characteristics, including, for example, the annular flow regime, the dispersed flow regime, and froth flow regime, and others.

The existence of a particular flow regime is known to be influenced by a variety of factors, including, for example, a gas void fraction in the fluid flow, an orientation of the flowtube 215 (e.g., vertical or horizontal), a diameter of the flowtube 215, the materials included within the two-phase flow, and the velocities (and relative velocities) of the materials within the two phase flow. Depending on these and other factors, a particular fluid flow may transition between several flow regimes over a given period of time.

Information about phase slip may be determined at least in part from flow regime knowledge. For example, in the bubble flow regime, assuming the bubbles are uniformly distributed, there may be little relative motion between the phases. Where the bubbles congregate and combine to form a less uniform distribution of the gas phase, some slippage may occur between the phases, with the gas tending to cut through the liquid phase.

In FIG. 2, a flow regime determination system 275 is included that has access to a database 280 of flow regime maps. In this way, information about an existing flow regime, including phase slip information, may be obtained, stored, and accessed for use in simultaneously determining liquid and gas mass flow rates within a two-phase flow.

In FIG. 2, it should be understood that the various components of the digital transmitter 104 are in communication with one another, although communication links are not explicitly illustrated, for the sake of clarity. Further, it should be understood that conventional components of the digital transmitter 104 are not illustrated in FIG. 2, but are assumed to exist within, or be accessible to, the digital transmitter 104. For example, the digital transmitter 104 will typically include (bulk) density and mass flow rate measurement systems, as well as drive circuitry for driving the driver 210.

Figure 3:
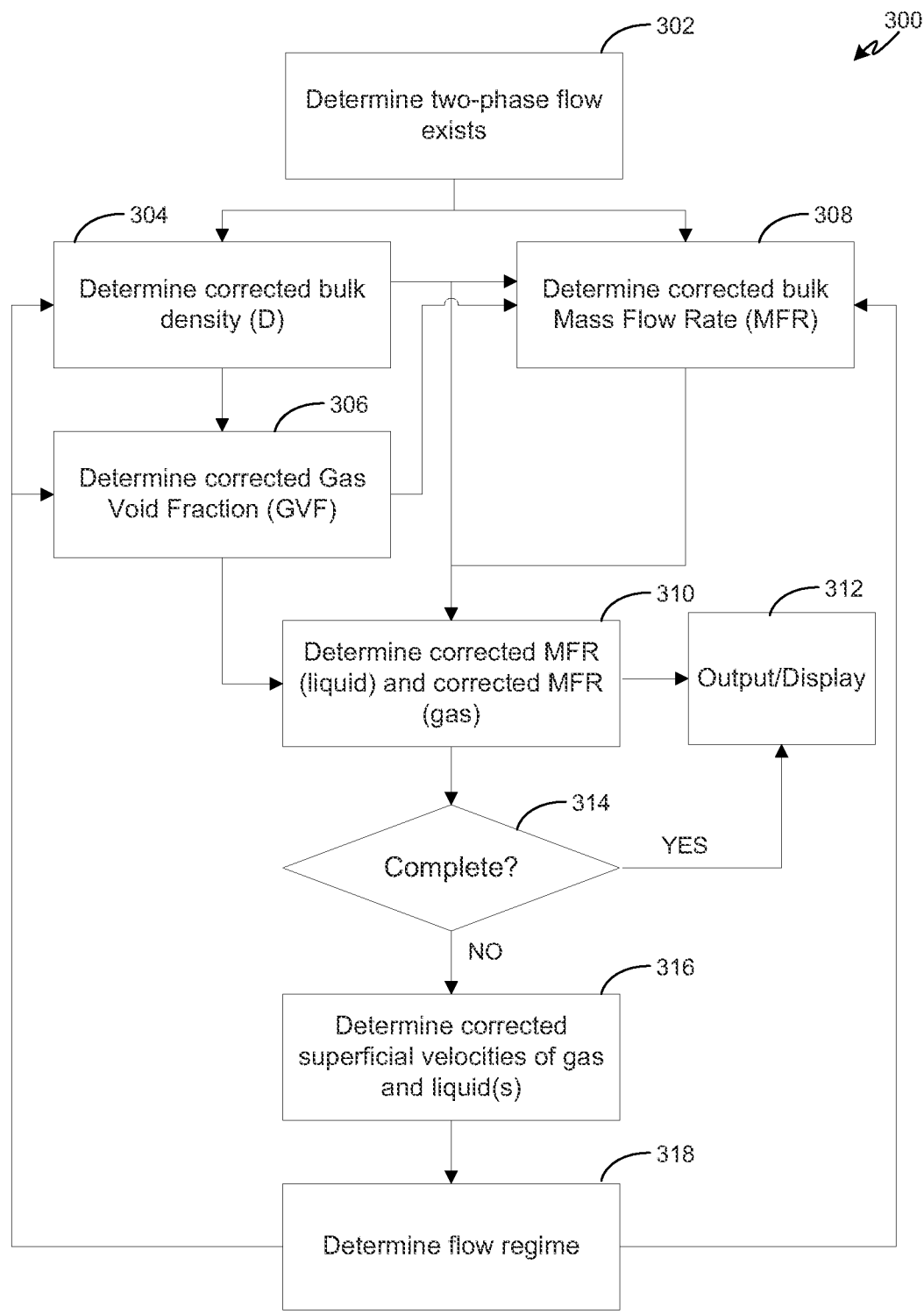
FIG. 3 is a flowchart illustrating an operation of the Coriolis flowmeter of FIG. 2.

FIG. 3 is a flowchart 300 illustrating an operation of the Coriolis flowmeter 200 of FIG. 2. Specifically, FIG. 3 illustrates techniques by which the flowmeter 200 of FIG. 2 is operable to simultaneously determine liquid and gas flow rates $MF_{liquid}$ and $MF_{gas}$ for a two-phase flow. In FIG. 3, it is determined that a gas/liquid two-phase flow exists in the flowtube 215 (302). This can be done, for example, by an operator during configuration of the mass flowmeter/densitometer for gas/liquid flow. As another example, this determination may be made automatically by using a feature of the Coriolis flowmeter to detect that a condition of two-phase gas-liquid flow exists. In the latter case, such techniques are described in greater detail in, for example, U.S. Pat. No. 6,311,136 and U.S. Pat. No. 6,505,519, incorporated by reference above.

Once the existence of two-phase flow is established, a corrected bulk density $\rho_{corrected}$ is established (304) by the density correction system 240, using the density correction database 245 of the transmitter 104. That is, an indicated density $\rho_{apparent}$ is corrected to obtain $\rho_{corrected}$. Techniques for performing this correction are discussed in more detail below. Once $\rho_{corrected}$ is determined, a corrected gas void fraction $\alpha_{corrected}$ may be determined (306) by the void fraction determination/correction system 260. Also, a corrected bulk mass flow rate $MF_{corrected}$ is determined (308) by the mass flow rate correction system 250. As with density, techniques for obtaining the corrected void fraction $\alpha_{true}$ and mass flow rate $MF_{corrected}$ are discussed in more detail below.

In FIG. 3, it should be understood from the flowchart 300 that the determinations of $\rho_{corrected}$, $\alpha_{corrected}$ and $MF_{corrected}$ may occur in a number of sequences. For example, in one implementation, the corrected void fraction $\alpha_{corrected}$ is determined based on previously-calculated corrected density $\rho_{corrected}$, whereupon the corrected mass flow rate $MF_{corrected}$ is determined based on $\alpha_{corrected}$. In another implementation, $\alpha_{corrected}$ and $\rho_{corrected}$ may be calculated independently of one another, and/or $\rho_{corrected}$ and $MF_{corrected}$ may be calculated independently of one another.

Once corrected density $\rho_{corrected}$, corrected void fraction $\alpha_{corrected}$, and corrected mass flow rate $MR_{corrected}$ are known, then the mass flow rates of the gas and liquid components are determined (310) by the flow component mass flow rate determination system 265. Techniques for determining the liquid/gas component flow rates are discussed in more detail below with respect to FIG. 4.

Once determined, the liquid/gas component flow rates may be output or displayed (312) for use by an operator of the flowmeter. In this way, the operator is provided, perhaps simultaneously, with information about both the liquid mass flow rate $MF_{liquid}$ and the gas mass flow rate $MF_{gas}$ of a two-phase flow.

In some instances, this determination may be sufficient (314), in which case the outputting of the liquid/gas component flow rates completes the process flow. However, in other implementations, the determination of the individual component mass flow rates may be improved upon by factoring in information about, for example, the superficial velocities of the gas/liquid components, the flow regime(s) of the flow, and phase slip, if any, between the components.

In particular, superficial velocities of the gas and liquid, $SV_{gas}$ and $SV_{liquid}$ are determined as follows. Gas superficial velocity $SV_{gas}$ is defined as:

$$SV_{gas} = MF_{gas}/(\rho_{gas} * A_T) \qquad \text{Eq. 1}$$

where the quantity $A_T$ represents a cross-section area of the flowtube 215, which may be taken at a point where a void fraction of the flow is measured. Similarly, a liquid superficial velocity $SV_{liquid}$ is defined as:

$$SV_{liquid} = MF_{liquid}/(\rho_{liquid} * A_T) \qquad \text{Eq. 2}$$

As shown in Eqs. 1 and 2, determination of superficial velocities in this context relies on the earlier determination of $MF_{gas}$ and $MF_{liquid}$. It should be understood from the above description and from FIG. 3 that $MF_{gas}$ and $MF_{liquid}$ represent corrected or true mass flow rates, $MF_{gas}^{corrected}$ and $MF_{liquid}^{corrected}$ since these factors are calculated based on $\rho_{true}$, $\alpha_{true}$, and $MF_{true}$. As a result, the superficial velocities $SV_{gas}$ and $SV_{liquid}$ represent corrected values $SV_{gas}^{corrected}$ and $SV_{liquid}^{corrected}$. Further, the density values $\rho_{gas}$ and $\rho_{liquid}$ refer, as above, to known densities of the liquid and gas in question, which may be stored in the density correction database 245. As discussed in more detail below with respect to techniques for calculating corrected density $\rho_{corrected}$, the density values $\rho_{gas}$ and $\rho_{liquid}$ may be known as a function of existing temperature or pressure, as detected by temperature sensor 220 and pressure sensor 225.

Using the superficial velocities and other known or calculated factors, some of which may be stored in the flow regime maps database 280, a relevant flow regime and/or phase slip may be determined (318) by the flow regime determination/correction system 275. Once superficial velocities, flow regime, and phase slip are known, further corrections may be made to the corrected bulk density $\rho_{true}$, corrected bulk mass flow rate $MF_{corrected}$, and/or corrected void fraction $\alpha_{corrected}$. In this way, as illustrated in FIG. 3, component flow rates $MF_{gas}$ and $MF_{liquid}$ may be determined.

Flow regime(s) in two phase liquid/gas flow may be described by contours on a graph plotting the liquid superficial velocity versus the gas superficial velocity. As just described, an improvement to determinations of $\rho_{corrected}$, $\alpha_{corrected}$, and/or $MF_{corrected}$ may be obtained by first establishing an approximate value of the liquid and gas flow rates, and then applying a more detailed model for the flow regime identified. For example, at relatively low GVF and relatively high flow there exists a flow regime in which the aerated fluid behaves as a homogenous fluid with little or no errors in both density and mass flow. This can be detected as homogenous flow requiring no correction, simply using observation of the drive gain, which shows little or no increase in such a setting, despite a significant drop in observed density.

Figure 4:
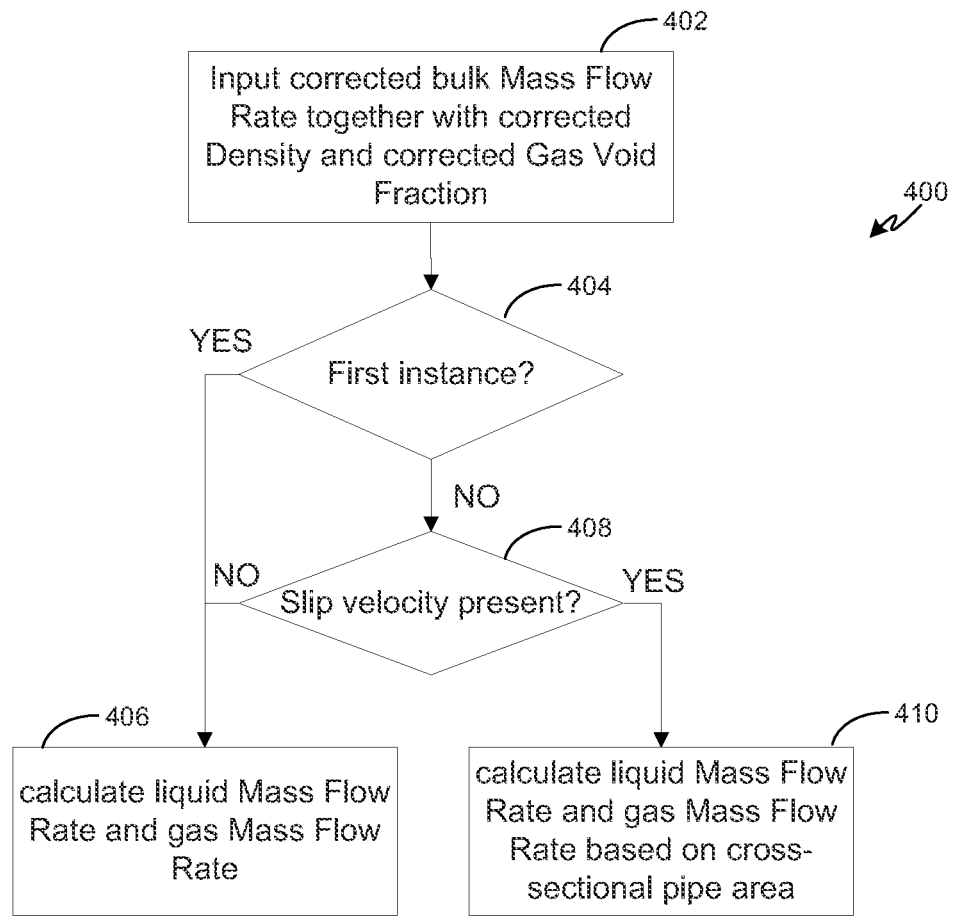
FIG. 4 is a flowchart illustrating techniques for determining liquid and gas flow rates for a two-phase flow.

FIG. 4 is a flowchart 400 illustrating techniques for determining liquid and gas flow rates $MF_{liquid}$ and $MF_{gas}$ for a two-phase flow. That is, the flowchart 400 generally represents one example of techniques for determining liquid and gas flow rates (310), as described above with respect to FIG. 3.

In FIG. 4, the determination of liquid and gas flow rates (310) begins with inputting the corrected density, void fraction, and mass flow rate factors $\rho_{corrected}$, $\alpha_{corrected}$, and $MF_{corrected}$ (402). In a first instance, (404), the liquid and gas flow rates are determined (406) using Eqs. 3 and 4:

$$MF_{gas} = \alpha_{corrected}(\rho_{gas}/\rho_{true})(MF_{corrected}) \qquad \text{Eq. 3}$$

$$MF_{liquid} = (1-\alpha_{corrected})(\rho_{liquid}/\rho_{corrected})(MF_{corrected}) \qquad \text{Eq. 4}$$

Eqs. 3 and 4 assume that there is no slip velocity (i.e., phase slip) between the liquid and gas phases (i.e., average velocity of the gas phase, $AV_{gas}$, and average velocity of the liquid phase, $AV_{liquid}$, are equal). This assumption is consistent with the fact that, in the first instance, superficial velocities and flow regimes (and therefore, phase slip) have not been determined. In the second instance and thereafter (404), a determination is made, perhaps by the flow regime determination/correction system 275, as to whether phase slip exists (408). If not, then Eqs. 3 and 4 are used again (406) or the process ends.

If phase slip does exist (408), defined above as $S = AV_{gas}/AV_{liquid}$, the terms $MF_{gas}$ and $MF_{liquid}$ are calculated using the cross-sectional area of the flowtube 215, $A_T$, as also used in the calculation of superficial velocities in Eqs. 1 and 2 (410). Using the definition of slip S just given, $$MF_{gas} = \rho_{gas}(\alpha_{corrected} A_T)(AV_{gas}) = \rho_{gas}(\alpha_{corrected} A_T)(S)(AV_{liquid}) \qquad \text{Eq. 5}$$

$$MF_{liquid} = \rho_{liquid}((1-\alpha_{corrected})A_T)(AV_{liquid}) \qquad \text{Eq. 6}$$

Since $MF_{corrected} = MF_{gas} + MF_{liquid}$, Eqs. 5 and 6 may be solved for $AV_{liquid}$ to obtain Eq. 7:

$$AV_{liquid} = MF_{true}/(A_T(\rho_{gas}\alpha_{corrected} + \rho_{liquid}(1-\alpha_{corrected}))) \qquad \text{Eq. 7}$$

As a result, the liquid and gas flow rates are determined (406) using Eqs. 8 and 9:

$$MF_{liquid} = [\rho_{liquid}(1-\alpha_{corrected})/(\rho_{gas}\alpha_{corrected} + \rho_{liquid}(1-\alpha_{corrected}))][MF_{corrected}] \qquad \text{Eq. 8}$$

$$MF_{gas} = MF_{corrected} - MF_{liquid} \qquad \text{Eq. 9}$$

As described above, gas entrained in liquid forms a two-phase flow. Measurements of such a two-phase flow with a Coriolis flowmeter result in indicated parameters $\rho_{apparent}$, $\alpha_{apparent}$, and $MF_{apparent}$ for density, void fraction, and mass flow rate, respectively, of the two-phase flow. Due to the nature of the two-phase flow in relation to an operation of the Coriolis flowmeter, these indicated values are incorrect by a predictable factor. As a result, the indicated parameters may be corrected to obtain actual parameters $\rho_{corrected}$, $\alpha_{corrected}$, and $MF_{corrected}$. In turn, the actual, corrected values may be used to simultaneously determine individual flow rates of the two (gas and liquid) components.

The above discussion provides examples of measuring component mass flow rates in a two-phase flow. Flowmeters also may be used to measure further mixed flows. For example, a "three-phase" flow or "mixed two-phase flow" refers to a situation in which two types of liquid are mixed with a gas. For example, a flowing mixture of oil and water may contain air (or another gas), thus forming a "three-phase flow," where the terminology refers to the three components of the flow, and does not generally imply that a solid material is included in the flow. However, in some examples, a multi-phase fluid may include a solid material, such as sand.

Figure 5A:
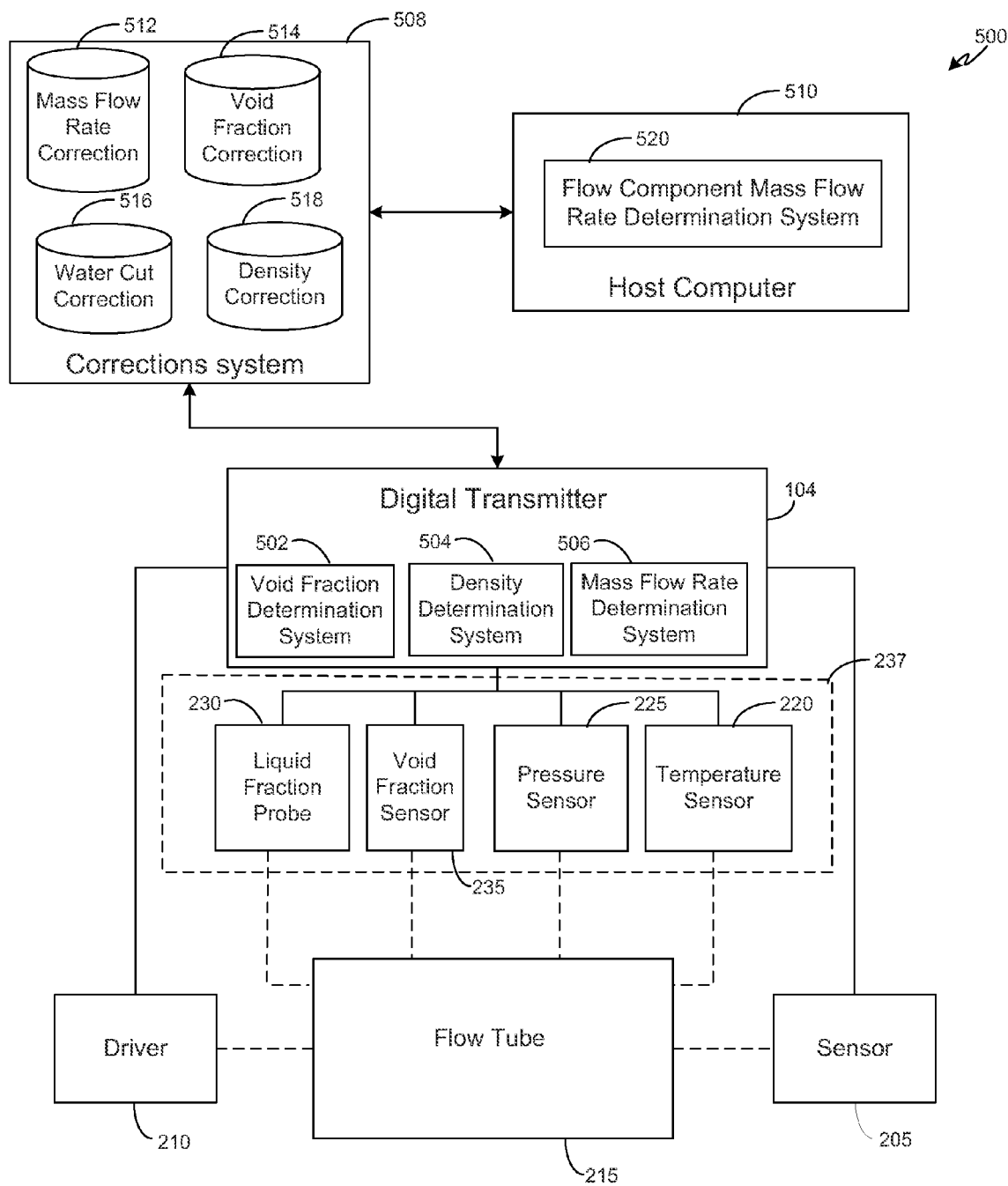
FIG. 5A is a block diagram of a Coriolis flowmeter.

FIG. 5A is a block diagram of a flowmeter system 500. The flowmeter system 500 may be used, for example, to determine individual component flow rates within a three-phase flow. For example, the system 500 may be used to determine a mass flow rate of a gas component and a mass flow rate of a liquid component (e.g., a component of the three-phase flow that includes oil and water) of the three-phase flow. Additionally, the system 500 may be used to determine an amount of oil or a portion of oil within an oil, water, and gas flow that travels through a pipe at an oil extraction facility during a given period of time.

The flowmeter system 500 also may be used to obtain accurate measurements from the digital transmitter 104, such as, for example, density measurements or mass flow rate measurements. The system 500 also may be used, for example, to obtain an improved measurement from an external sensor, such as, for example, the liquid fraction probe 230, or the void fraction sensor 235, relative to what measurements might be obtained using the external sensor(s) alone.

In FIG. 5A, the digital transmitter 104 includes a void fraction determination system 502, a density determination system 504, and a mass flow rate determination system 506 (in addition to a number of components that are not shown for clarity's sake, e.g., a drive signal generator, or a multi-phase detection system, or any of the components illustrated or discussed with respect to FIG. 2). That is, as should be understood from the above description, the systems 502, 504, and 506 may be used to measure corresponding parameters of a fluid flow within the flow 210. Further, as also explained above, to the extent that the fluid flow contains gas and/or mixed liquids, the measurements output by the systems 502, 504, and 506 generally represent raw or apparent values for the corresponding parameters, which ultimately may be corrected with a corrections system 508.

For example, an apparent mass flow rate of a three-phase fluid flow within the flowtube 215 may be output to the corrections system 508 for correction using a mass flow rate correction module 512, while an apparent density of the three-phase fluid flow within the flowtube 215 may be output to the corrections system 508 for correction using a density correction module 518. Somewhat similarly, a measurement or determination of an apparent void fraction within the fluid flow may be corrected using a density correction module 514, while a measurement or determination of an apparent liquid fraction (e.g., water cut from probe 230) may be corrected using a water cut correction module 516. As described in more detail below, the various correction modules 512-518 may work in conjunction with one another, and/or with other components, in order to obtain their respective corrected values.

Once obtained, corrected values such as mass flow rate, density, water cut, or void fraction (or some combination thereof) may be output to a host computer 510 for determination of individual mass flow rates of each of the three components of the three-phase fluid flow, using a component flow rate determination system 520. As a result, and as referenced above, individual flow rates and/or amounts of each of the three components may be determined.

More generally, an example of the system 500 includes three general elements used to obtain corrected measurement values and/or individual component flow rates: the transmitter 104, one or more of the individual external sensors identified generically with a reference numeral 522, and one or more elements of the corrections system 508. Of course, many combinations, variations, and implementations of these elements may be used, various examples of which are discussed in more detail below.

For example, in some implementations, the digital transmitter 104 may not include the void fraction determination system 502. In some cases, the void fraction determination system 502 may be included with, or associated with, the liquid fraction probe 230, or may be unneeded depending on a type or configuration of the void fraction sensor 235. In such cases, to the extent that it is needed, the void fraction may be determined from outputs of the correction modules 512, 516, and/or 518.

Further, although the external sensors 522 are shown in FIG. 5A to be in communication with the digital transmitter 104 and the flowtube 215, it should be understood that the external sensors 522 may obtain their respective measurements in a number of different ways. For example, examples of the temperature sensor 220, the pressure sensor 225, and the void fraction sensor 230 are described above, with respect to, for example, FIG. 2. Further, the liquid fraction probe 235 may be in series with the flowtube 215 with respect to a primary pipe for transporting the three-phase fluid flow, and may maintain separate communication with the transmitter 104, the corrections system 508, and/or the host computer 510.

In FIG. 5A, the corrections system 508 is shown as being separate from the digital transmitter 104 and the host computer 510. In some implementations, however, the corrections system 508 may be located within the digital transmitter 104, the host computer 510, or may be associated with one or more of the external sensors 522. In still other implementations, portions of the corrections system 508 may be included within different sections of the system 500. For example, density and mass flow rate corrections may be performed at the digital transmitter 104, while water cut corrections may be performed at the liquid fraction probe 230.

In some implementations, the corrections system 508 may include all of the modules 512-518 (as shown), or some subset thereof, or may include other modules, not specifically illustrated in FIG. 5A (e.g., a corrections module for correcting a density of the two-liquid component within the three-phase flow, such as the oil/water mixture in an oil/water/gas fluid flow). Further, some or all of any such correction modules may be integrated with one another. For example, the mass flow rate and density corrections may be incorporated into one module, while the water cut correction module 516 may be separate.

Along the same lines, it should be understood that the component flow rate determination system 520 may be situated in a number of places within the system 500. For example, the component flow rate determination system 520 may be located within the corrections system 508, or may be located within the digital transmitter 104.

Various examples of the above and other implementations, as well as examples of specific techniques for obtaining corrected flow measurements and individual component flow rates, are described in more detail below. In general, however, it should be understood that the system 500 and other implementations thereof allows for all or substantially all of the three-phase fluid flow to flow continuously through the flowtube 215 and through an associated pipe or other conduit for transporting the three-phase flow material.

As a result, determinations of individual component flow rates do not require separation of the three-phase fluid flow into separate flows containing one or more of the constituent components. For example, when the three-phase flow contains oil, water, and gas, it is not necessary to separate the gas from the oil/water liquid combination in order to perform measurements (e.g., mass flow rate) on the oil portion of the resulting oil/liquid flow. Accordingly, reliable measurements of an amount of oil produced, for example, at an oil production facility, may be made easily, quickly, inexpensively, and reliably.

Figure 5B:
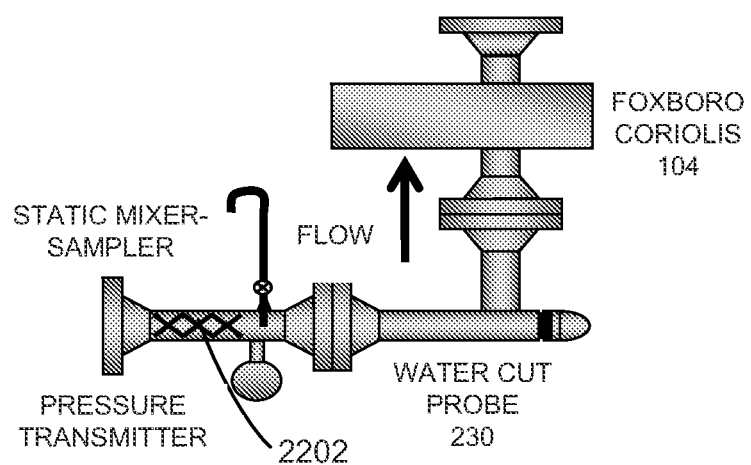
FIG. 5B is a diagram of an implementation of the system of FIG. 5A.

FIG. 5B is a diagram of an implementation of the system 500 of FIG. 5A. In FIG. 5B, the liquid fraction probe 230 is illustrated as a water cut probe that is in series with the digital transmitter 104 with respect to three-phase fluid flow through a pipe 2202. In the implementation shown in FIG. 5B, the three-phase fluid flows upward through the Coriolis flowmeter 104.

Figure 6:
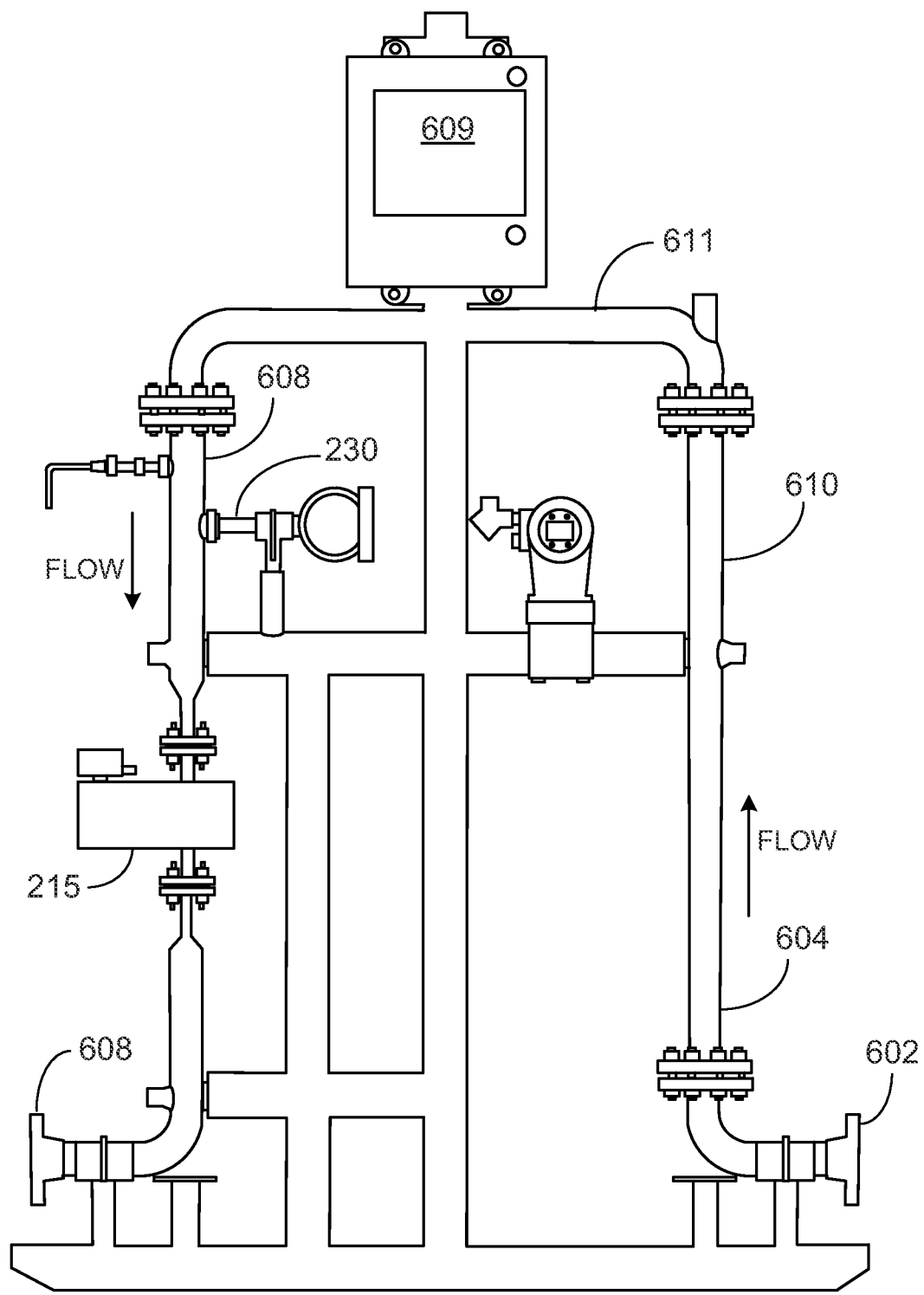
FIG. 6 is an illustration of another implementation of the system of FIG. 5A.

FIG. 6 is a diagram of another implementation of the system 500 of FIG. 5A. In this implementation, the liquid fraction probe 230 is in series with the flowtube 215, and fluid flows downward through the flowtube 215 and the liquid fraction probe 230. The fluid may be a three-phase fluid, such as a fluid that includes two liquid phases, such as a water phase and an oil phase, and a gas phase. The system 600 includes an inlet 602 though which fluid flows into a pipe 604, the liquid fraction probe 230, the flowtube 215, and an outlet 608 though which fluid flows out of the pipe 604. The system 600 also includes an interface module 609, which may include an electronic processor, an electronic storage (such as a memory), and one or more input/output modules (such as a display, a communications interface for connection to a transmitter in communication with the flowtube 215 (such as the transmitter 104) and/or connection with the liquid fraction probe 230, and/or for connection to a remote terminal (not shown), and a tactile manual input, such as a keyboard and a mouse).

The liquid fraction probe 230 may be a watercut meter (or watercut probe) that measures and provides an estimate of the fraction of water in the fluid that flows through the water cut meter. The fraction of water may be referred to as the water cut. In the system 600, the flowtube 215 is placed such that the fluid flows through the Coriolis flowmeter in a downward direction that corresponds to the direction of gravity.

In some applications, such as mature oil and gas wells in which the fluid that flows in the pipe 604 has a relatively low pressure and a relatively high gas void fraction (GVF), the fluid may pass through the Coriolis flowmeter as a series of slugs that include mostly gas (and thus have a high GVF) or mostly liquid (and thus have a low GVF). In some applications, such as monitoring the output of wells in depleted or low pressure oil and gas reservoirs, the multi-phase stream to be measured may include a low pressure stream with high GVF. In these conditions, better measurement performance may be obtained from the multiphase measurement system if the three-phase mixture passes though in a series of slugs of either very high GVF and made almost entirely of gas or relatively low GVF and made almost entirely of liquid.

Accordingly, an arrangement of the Coriolis flowmeter and the water cut probe, such as that shown in FIG. 6, may be employed to facilitate slug flow. As compared to a substantially steady fluid stream of separated liquid with an intermediate GVF, a fluid stream that includes liquid or gas slugs may be more efficiently measured with a Coriolis flowmeter. When a slug of pure, or substantially pure liquid (for example, the slug includes 95% or more of liquid, passes through the liquid fraction probe 230 and the flowtube 215, there may be redundant information. For example, when a liquid slug passes through the flowtube 215, measurement data to resolve three phases (such as gas, oil, and water) may be obtained by the Coriolis flowmeter and watercut meter, but only two phases (such as water and oil) are present. Alternative calculation methods for the water and oil flow rates may be used for this condition, and the redundant measurement information may be used to provide cross-checking between the Coriolis flowmeter and the liquid fraction probe 230, as described below in FIGS. 7 and 8. Such cross-checking may provide an indication of a malfunction or other problem with the Coriolis flowmeter or the liquid fraction probe 230.

The system 600, which may be referred to as the skid 600, may be used in low pressure, low liquid flow applications, such as a mature oil and gas wells. In the example shown in FIG. 6, the liquid fraction probe 230 and the flowtube 215 are in a downward orientation on a downward leg 608 of the skid 600. Placement of the liquid fraction probe 230 and the flowtube 215 in a downward orientation may be beneficial in low pressure, high GVF applications. For example, as compared to a system in which the Coriolis flowmeter is oriented such that fluid flows in the upward direction through the flowtube 215, positioning the flowtube 215 such that fluid flows downward through the flowtube 215 may result in the Coriolis flowmeter draining more effectively because gravity and any gas flow work in the same direction. Additionally, separation of gas and liquid phases of the multi-phase fluid may occur naturally on the upward leg 610 of the skid 600 because gas passes through the flowtube 215 at any time, whereas liquid tends to collect in the upward leg 610 until a sufficiently large slug of liquid is capable of passing through a top section 611 of the skid 600 to the downward leg 608. Once the liquid has passed through the flowtube 215, gravity acts to minimize, or eliminate, liquid flow back into the flowtube 215. In some implementations, a device to further minimize backwash into the flowtube 215, such as a non-return valve (not shown), may be included in the skid 600. Thus, the arrangement shown in FIG. 6 may encourage slug flow.

Additionally, an arrangement such as shown in FIG. 6 may reduce the possibility of the flowtube 215 being in a partially filled state (or partially filled condition). For example, when liquid flow completely or nearly stops, as may occur for extended periods of time for a low-producing oil and gas well, unless the flowtube 215 drains completely, the flowtube 215 may enter a partially filled state. While in a partially filled state, the flowtube 215 may produce a spurious (in inaccurate), non-zero mass flow reading, which in turn may lead to false readings of oil and water flows through the flowtube 215. A partially filled state may be detected independently of detecting the absence of fluid flow. For example, a partially filled state may be detected using a density cutoff such that if the density reported by the transmitter 104 is below the density cutoff, the liquid flowrates provided by the transmitter 104 are set to zero. The cutoff may be, for example, 100 kg/m³. In some implementations, another measurement, such as a measurement from a differential pressure meter, may be used to detect the presence of liquid flow. A sufficiently high differential pressure across a section of the skid 600 (such as the pressure across the flowtube 215, across the entire skid 600, or an across another component, such as an orifice plate in the skid) may indicate the presence of fluid flow. In some implementations, a flow switch (not shown) may be used to detect the presence or absence of liquid flow. However, the arrangement shown in FIG. 6 reduces or eliminates the possibility of liquid being trapped within the flowtube 215, thus reducing or eliminating the occurrence of a partially filled state and the effects of a partially filled state. Moreover, in at least some instances, the arrangement of the flowtube 215 on the downward leg 608 encourages slug flow, and as discussed above, measurements based on slug flow may be more accurate than measurements based on an equivalent non-slug flow. In some implementations, the liquid fraction probe 230 (which may be a water cut meter) may be able to detect that no liquid is in the liquid fraction probe 230. Such an indicator from the liquid fraction probe 230 (which may be a water cut meter) may be used as a flag or indicator to cut off or ignore spurious flow readings from the Coriolis flowmeter.

Figure 7:
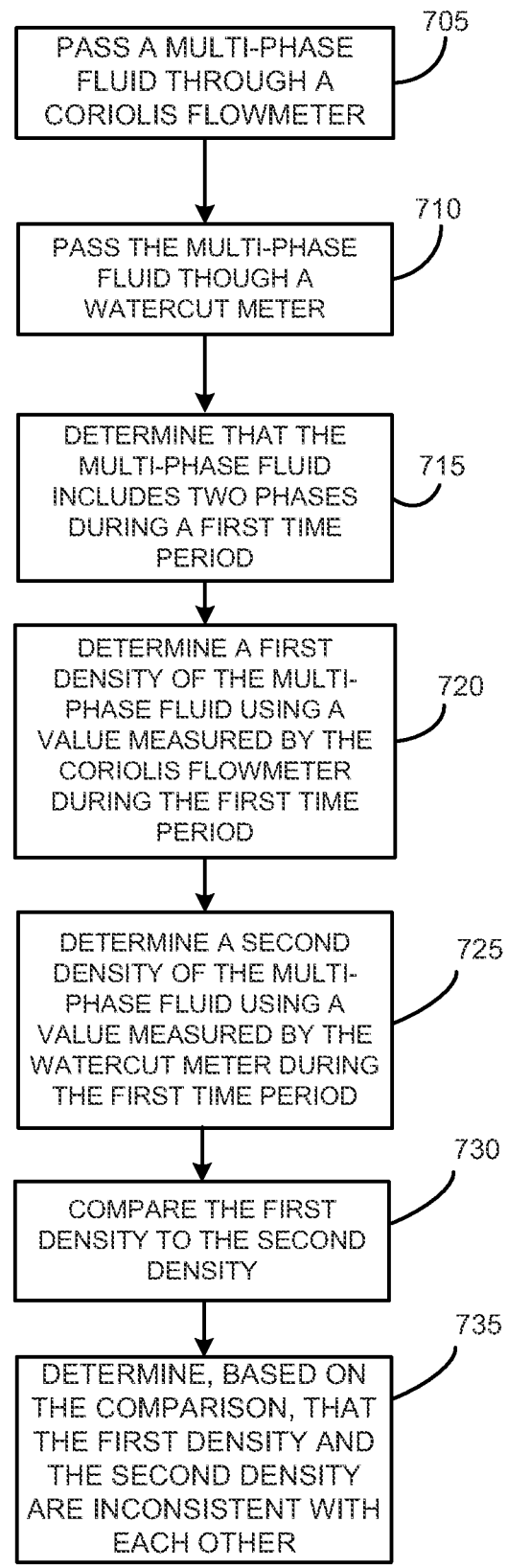
FIGS. 7 and 8 show example processes for determining whether an inconsistency exists between a Coriolis flowmeter and a water cut meter.

FIG. 7 shows an example process 700 that may be used to cross-check a Coriolis flowmeter and a water cut probe. The process 700 may be performed using data from the system 600, however, this is not necessarily the case. The process 700 may be performed by the transmitter 104, or the process 700 may be performed by a processor (such as a processor in a flow computer) that is external to, but in communication with, the transmitter 104. In some implementations, some portions of the process 700 may be performed by the transmitter 104 and some portions may be performed by a processor that is external to the transmitter 104. The processor that is external to the transmitter 104 may be a processor included in the interface module 609.

The process 700 uses redundancies in measurements produced by the transmitter 104 and the liquid fraction probe 230 that exist when the fluid that passes through the flowtube 215 and the liquid fraction probe 230 is a pure, or substantially pure, liquid. For example, the fluid may be substantially pure when the fluid includes more than 95% liquid. The fluid may be purely liquid when liquid slugs that include, for example, an oil phase and a water phase, but not a gas phase, flow through the liquid fraction probe 230 and the flowtube 215. When a slug of pure liquid passes through the liquid fraction probe 230 and the flowtube 215, and measurement data to resolve three phases (oil, gas, water) is available but only two phases (oil, water) are present, each of the flowmeter 104 and the liquid fraction probe 230 may produce redundant information that may be used to cross-check the data obtained from the transmitter 104 with that obtained from the liquid fraction probe 230. Cross-checking the Coriolis flowmeter with, for example, a water cut probe may be used to identify a malfunction in either or both of the Coriolis flowmeter and the water cut probe and/or to identify an incorrect assumption in a preset or preconfigured system parameter, such as an assumed water or oil density.

Referring to FIG. 7, a multi-phase fluid is passed through the flowtube 215 (705), and the multi-phase fluid is passed through the liquid fraction probe 230 (710). The multi-phase fluid includes two phases during a first time period and three phases during a second time period. For example, the multi-phase fluid may include an oil phase and a water phase during the first time period, and an oil phase, a water phase, and a gas phase during a second time period. Thus, during the first time period, the multi-phase fluid may considered to be a liquid, or nearly liquid, slug and may be considered to be free of gas and to have a very low GVF (for example, a GVF lower than 5%). In some implementations, the first time period is long enough to provide for multiple measurements to be obtained from the liquid fraction probe 230 and the transmitter 104. For example, the first time period may be of a duration that corresponds to ten measurements or ten measurement updates. A measurement may occur, for example, approximately every second. Thus, the first time period may be a time that is about ten seconds or greater. As discussed in below, in some implementations, the measurements from the transmitter 104 and the liquid fraction probe 230 taken during a time period may be filtered to reduce noise and improve accuracy and performance, thus, multiple measurements taken during the first time period may improve accuracy.

It is determined that the multi-phase fluid includes two phases during the first time period (715). In some examples, the two phases may be oil and water, thus the multi-phase fluid is substantially free of gas. The multi-phase fluid may be deemed to be free of gas when a low drive gain reading is obtained from the Coriolis flowmeter. For example, a drive gain of 0.05 or less may be considered to be a low drive gain that indicates that the multi-phase fluid is free gas. A low drive gain is indicative of a flow that includes only liquid or only gas. Additionally, or alternatively, a density reading from the transmitter 104 may provide an indication as to whether a low drive gain may be attributed to the presence of a pure liquid. For example, a density reading of greater than about 700 kg/m³ strongly indicates that the fluid is a pure liquid, whereas a density reading less than about 100 kg/m³ indicates that the fluid is a pure gas, depending on the pressure conditions at the point of density measurement.

A first value of a parameter of the multi-phase fluid is determined using information from the transmitter 104 (720), and a second value of the parameter of the multi-phase fluid is determined using information from the liquid fraction probe 230 (725). The parameter may be, for example, a liquid density or a watercut (e.g., a fraction or percentage of the flow that is water). The first value of the parameter is compared to the second value of the parameter (730). Based on the comparison, it is determined whether the first value of the parameter and the second value of the parameter are inconsistent with each other (735). As discussed in greater detail below, inconsistencies between the first value of the parameter and the second value of the parameter indicate that either the Coriolis transmitter 104 or the liquid fraction probe 230 are malfunctioning or that certain assumed and preconfigured values, such as liquid density or oil density, are inaccurate.

In greater detail, in some circumstances where the drive gain, density and perhaps other signals indicate a pure liquid mixture, there may be redundancy between the readings provided by the Coriolis flowmeter (such as the transmitter 104 that is coupled to the flowtube 215) and a water cut meter (such as the liquid fraction probe 230). For example, with no, or very little, gas in the flow stream, an estimate of the water cut based upon Coriolis flowmeter readings only, $\delta_{wC}$ may be determined as follows:

$$\delta_{wC} = \frac{(\rho_m - \rho_o)}{(\rho_w - \rho_o)} \times 100\% \qquad \text{Eq. 10}$$

In Equation 10, $\rho_o$ is the oil density (assumed known), $\rho_w$ is the water density (assumed known), and $\rho_m$ as the mixture density measured by the Coriolis flowmeter. The estimate of the watercut based on the Coriolis flowmeter readings may be compared against the reading obtained from the water cut meter $\delta_{wW}$ (also as a percentage). Instances where a significant difference (such as, for example 5%) may be indicative of an inconsistency.

In some implementations, an estimated liquid density is calculated based on the readings from the water cut, using $$\rho_{mW} = \frac{\delta_{wW}}{100} * \rho_w + \left(1 - \frac{\delta_{wW}}{100}\right) * \rho_o. \qquad \text{Eq. 11}$$

The Coriolis flowmeter density reading of the mixture (e.g., the two-phase liquid slug) $\rho_m$ may be compared with the density estimate from Equation 11 based on the water cut reading. ($\rho_{mW}$).

Regardless of the parameter that is compared, a significant difference between the values obtained using the water cut meter and the values obtained using the Coriolis flowmeter readings may indicate an inaccuracy in the assumed value of $\rho_o$ or the assumed value of $\rho_w$ or may indicate a malfunction of the Coriolis flowmeter or the water cut meter. The amount of difference needed to indicate such an inaccuracy or malfunction may be determined, for example, experimentally.

In some implementations, further information may be used to determine which component is contributing to the inconsistency between the value of a parameter (such as density or water cut) determined using data from the Coriolis flowmeter and the value of the parameter determined using data from the water cut meter. For example, in applications where waxing or sand damage of the water cut meter is possible, the water cut meter may be considered the most likely source of the inconsistency. In another example, if the Coriolis flowmeter produces a density reading that is higher than the water density, particularly if a reading from the water cut meter indicates a nearly 100% portion of water, the assumed water density ($\rho_w$) is likely inaccurate. The assumed water density may be inaccurate when, for example, the salinity of the water in the multi-phase fluid changes unexpectedly. Similarly, if the Coriolis flowmeter reads a density that is lower than the oil density (particularly if this is reinforced by a near 0% reading from the water cut meter, indicating that the flow is nearly free of water), and assuming there is particularly strong evidence against the presence of gas, this suggests that the assumed oil density $\rho_o$ is not accurate.

Such a set of readings may trigger an alarm and/or a request to reconfigure, respectively, the assumed water density or the assumed oil density. In some implementations, the presence of readings indicating an inaccurate assumed or pre-configured water or oil density may trigger or cause an automatic adjustment of the assumed or pre-configured water or oil density. Additionally, the water cut meter is unlikely to generate measurements outside of the range of 0 to 100%, whereas the Coriolis-based calculation of water cut may fall below 0% or exceed 100% as a consequence of an inaccurate pre-configured density for water or oil. Accordingly, where the Coriolis flowmeter generates a water cut reading outside the range of 0 to 100%, comparison with the water cut meter may be bypassed. Thus, the presence of an inconsistency between a value of a parameter (such as density or watercut) determined based on data from the transmitter 104 and a value of the same parameter determined based on data from the liquid fraction probe 230, may indicate equipment malfunction or inaccuracy in certain assumed parameters.

The techniques discussed above may be employed during liquid-only conditions, which may occur sporadically during operation of a system such as the skid 600. To help mitigate against false detections of an inconsistency stemming from transient effects (such as a sudden and short-lived increase in the liquid in the multi-phase flow) rather than actual liquid-only conditions, the data used to determine whether an inconsistency exists may be tracked over time and filtered to remove transient effects. For example, the data collected from the transmitter 104 and the liquid fraction probe 230 may be updated at a measurement rate of, for example, 1 second. Accordingly, for a time period of, for example, 100 seconds, the data from the transmitter 104 and the liquid fraction probe 230, would form a time-series of 100 points (assuming that each measurement update was successfully completed). Because the time-series of data from the transmitter 104 and the liquid fraction probe 230 may be irregular due to transient effects, the time-series may be filtered by, for example, determining the mean (average) value of the time-series, determining the standard deviation of the time-series, and/or by determining the maximum and minimum value of the time-series. Determining the mean value of the time-series may remove spike values and ensure that decisions are based on data taken over a sufficiently long period of time. The standard deviation of a time-series of, for example, the difference between the Coriolis and watercut readings may show how much the difference varies over time. The minimum and maximum values may be used to diagnose inaccuracies with the assumed pure fluid densities.

Figure 8:
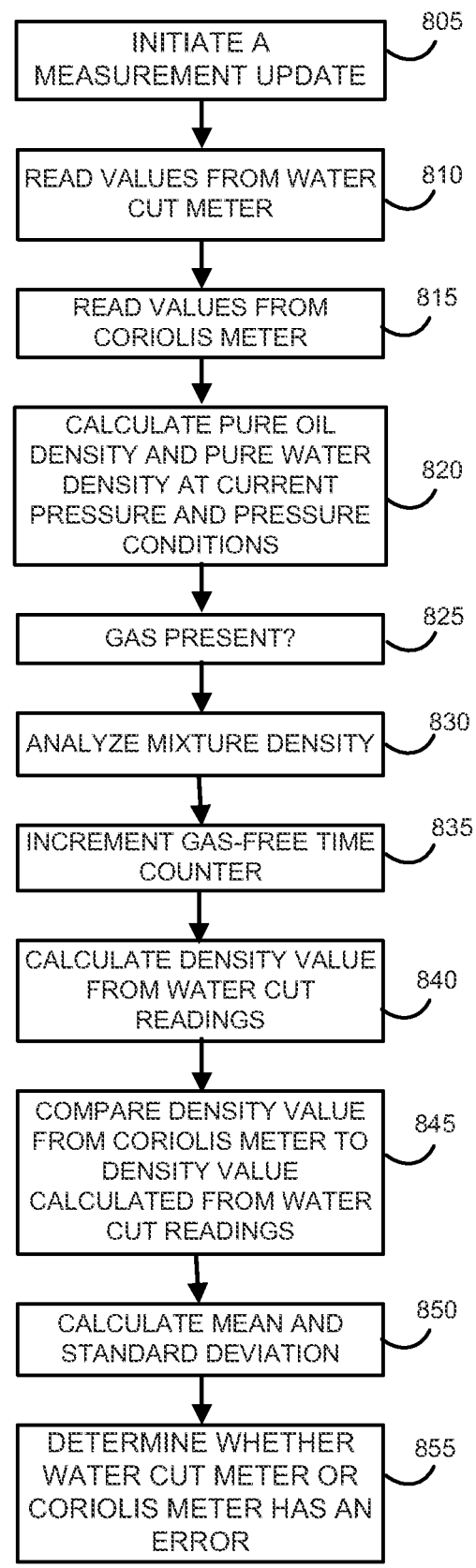

FIG. 8 shows another example process for determining whether an inconsistency between a density measured with the Coriolis flowmeter and a density determined using readings from the water cut meter is attributable to a malfunction in a water cut probe or a Coriolis flowmeter. The process 800 may be performed on a system such as the system 600. The process 800 may be performed by the transmitter 104, or the process 800 may be performed by a processor (such as a processor in a flow computer) that is external to the flowtube 215 and the liquid fraction probe 230 but in communication with the transmitter 104. In some implementations, some portions of the process 800 may be performed by the transmitter 104 and some portions may be performed by the processor that is external to the transmitter 104. The processor that is external to, but in communication with, the transmitter may be a processor included in the interface module 609.

A measurement update is initiated (805). Values are read from the water cut meter (810) and values are read from the Coriolis flowmeter (815). Values read from the water cut meter include a water cut reading (watercut_W) that represents a measurement of a percentage of the multi-phase fluid that is water. Values read from the Coriolis flowmeter include a density of the multi-phase fluid (dens_mix), a massflow (massflow_mix) of the multi-phase fluid, and a drive gain (drive_gain). If available, values of the pressure and temperature of the multi-phase fluid may also be read. The pure oil density (dens_o) is determined for current pressure and temperature conditions, and the pure water density (dens_w) is determined for current pressure and temperature conditions (820). The pure oil density (dens_o) and pure water density (dens_w) may be referred to as assumed or configured densities. In some implementations, rather than determine the pure oil density and pure water density from current pressure and temperature conditions, these densities are preset and stored, for example, in the processing interface 630.

Whether gas is present in the multi-phase fluid is determined (825). The presence of gas may be determined, for example, based on the drive gain obtained from the Coriolis flowmeter. If gas is present, the process 800 ends and the three-phase measurements discussed above with respect to FIG. 5 may be performed. If gas is not present, the density of the multi-phase fluid (dens_mix) read from the Coriolis flowmeter is analyzed (830). The density of the multi-phase fluid is compared to a preset threshold that is selected to indicate whether or not the density of the multi-phase fluid indicates that the multi-phase fluid is purely gas. For example, the threshold may be 750 kg/m$^3$, and if the density of the multi-phase fluid is less than the threshold, the multi-phase fluid is deemed to be not purely liquid and the process 800 ends.

Otherwise, the density of the fluid is greater than or equal to the threshold and is assumed to be purely liquid. The density of the multi-phase fluid is compared to the configured density of pure oil (dens_o). If the value of the observed density is less than the configured oil density, then the value of the observed density may be reported, presented and/or stored in an electronic storage medium, and the process 800 ends. In some implementations, an alarm is set to indicate that the configured density of pure oil may be incorrect. If the value of the observed density is greater than the configured oil density, the process 800 continues, and the value of the observed density is compared to the configured water density (dens_w). If the value of the observed density is greater than the configured water density, the observed density may be recorded, presented, and/or stored, and the process 800 ends. In some implementations, an alarm may be set to indicate that the configured water density may be incorrect. If the process 800 has not ended, the value of the observed density is between the configured oil density and the configured water density, and an estimate of the water cut may be reliably obtained.

A counter (time_gf) is incremented (835). Incrementing the counter indicates that another measurement of the multi-phase fluid without gas has occurred. The counter provides an indication of the amount of time data has been collected with a gas-free multi-phase fluid passing through the Coriolis flowmeter and the water cut meter. If sufficient time has passed (and, thus, sufficient gas-free measurements have been taken), a density value is determined based on the water cut reading from the water cut meter (840). In some implementations, 100 measurements may be the minimum number of measurements, in other implementations a minimum of 10 measurements may be the threshold. The density value determined based on the water cut reading is compared to the density value obtained from the Coriolis flowmeter (845). The comparison may be done for each measurement corresponding to an increment of the counter, and the comparison may be a percentage difference between the density observed by the Coriolis flowmeter and the density determined based on the readings from the water cut meter. The mean and standard deviation of the percentage difference may be determined (850).

Whether difference between the density observed by the Coriolis flowmeter and the density determined using readings from the water cut meter is attributable to a malfunction in the water cut meter or the Coriolis flowmeter is determined (855). In some implementations, the absolute value of the average difference between the two densities being greater then a threshold is an indication that water cut probe is experiencing an error. The threshold may be, for example, about 4%. In some implementations, if the standard deviation of the difference between the densities is greater than a threshold of, for example, 3%, an error may exist in the water cut probe.

Other implementations are within the scope of the claims.

What is claimed is:

1. A system comprising:
a watercut meter configured to receive a fluid; and
a Coriolis flowmeter coupled to the watercut meter, wherein the Coriolis flowmeter is configured to receive the fluid, and the flowmeter is oriented such that the fluid flows downward through the Coriolis flowmeter.

2. A system as set forth in claim 1 further comprising a fluidic system configured to fluidly connect the watercut meter and the Coriolis flowmeter in series between a system inlet and a system outlet.

3. A system as set forth in claim 2 wherein the fluidic system comprises a downward leg, the system being configured such that the fluid flows downward through the downward leg when the fluid flows from the inlet to the outlet, the Coriolis flowmeter being on the downward leg.

4. A system as set forth in claim 2 wherein the fluidic system comprises an upward leg, the system being configured such that the fluid flows upward through the upward leg when the fluid flows from the inlet to the outlet.

5. A system as set forth in claim 4 wherein the fluidic system is arranged such that the fluid flows through the upward leg before flowing through the watercut meter and before flowing through the Coriolis flowmeter.

6. A system as set forth in claim 3 wherein the watercut meter is on the downward leg and oriented such that the fluid flows downward through the watercut meter.

7. A system as set forth in claim 1 wherein the Coriolis meter comprises a flowtube having a flowtube inlet and a flowtube outlet, and wherein the Coriolis meter is mounted in the system such that the flowtube inlet is above the flowtube outlet.

8. A system as set forth in claim 1 further comprising a non-return valve positioned below the Coriolis meter to prevent backflow through the Coriolis meter.

9. A system as set forth in claim 1 further comprising a flow switch configured to detect the presence or absence of liquid flow.

10. A system as set forth in claim 1 further comprising an electronic processor and a communications interface for connecting the electronic processor with at least one of the watercut meter and the Coriolis flowmeter.

11. A system as set forth in claim 10 further comprising a differential pressure meter positioned to measure a differential pressure of the fluid across a portion of the system.

12. A system as set forth in claim 11 wherein the electronic processor is configured to determine whether or not there is liquid flow in the flowtube using the differential pressure meter.

13. A system as set forth in claim 10 wherein the electronic processor is configured to receive a watercut measurement from the watercut meter and a flow measurement from the Coriolis flowmeter.

14. A system as set forth in claim 13 wherein the electronic processor is configured to identify a malfunction in at least one of the watercut meter and the Coriolis meter by cross-checking the measurements from the watercut meter and the Coriolis meter.

15. A system as set forth in claim 10 wherein the electronic storage stores a density cutoff value.

16. A system as set forth in claim 15 wherein the Coriolis flowmeter is configured to report a measured density value to the electronic processor, and wherein the electronic processor is configured to compare the measured density value with the density cutoff value to detect a partially filled state in the Coriolis flowmeter when the density cutoff value exceeds the measured density value.

17. A system as set forth in claim 10 further comprising an interface module, the interface module including the electronic processor, the electronic storage, and an input/output device, the input/output device including the communications interface, a display and a tactile manual input.

* * * * *